(12) United States Patent
Sunada et al.

(10) Patent No.: US 8,883,511 B2
(45) Date of Patent: Nov. 11, 2014

(54) METHOD FOR EVALUATING CHEMICAL STABILITY OF POLYCHLOROPRENE LATEX

(75) Inventors: Kiyoshi Sunada, Itoigawa (JP); Takeo Mori, Itoigawa (JP)

(73) Assignee: Denki Kagaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/002,623

(22) PCT Filed: Mar. 2, 2012

(86) PCT No.: PCT/JP2012/055340
§ 371 (c)(1),
(2), (4) Date: Aug. 30, 2013

(87) PCT Pub. No.: WO2012/121135
PCT Pub. Date: Sep. 13, 2012

(65) Prior Publication Data
US 2013/0337573 A1 Dec. 19, 2013

(30) Foreign Application Priority Data

Mar. 10, 2011 (JP) .................................. 2011-053412

(51) Int. Cl.
*G01N 31/02* (2006.01)
*G01N 31/00* (2006.01)
*C08C 1/02* (2006.01)
*C08K 3/00* (2006.01)
*C08L 11/02* (2006.01)
*C08J 3/05* (2006.01)
*C08C 1/14* (2006.01)
*C08K 3/28* (2006.01)

(52) U.S. Cl.
CPC .............. *G01N 31/02* (2013.01); *C08K 3/0083* (2013.01); *C08J 2311/02* (2013.01); *C08L 11/02* (2013.01); *C08J 3/05* (2013.01); *C08K 2003/287* (2013.01); *C08C 1/14* (2013.01)
USPC ........................................................ 436/125

(58) Field of Classification Search
CPC .......... G01N 31/02; G01N 31/00; C08C 1/14; C08C 1/00
USPC ........................................................ 436/125
See application file for complete search history.

(56) References Cited

U.S. PATENT DOCUMENTS

| 6,034,173 A | 3/2000 | Rivet ............................. 524/834 |
| 8,436,102 B2 * | 5/2013 | Hashimoto et al. ........... 525/250 |
| 2002/0111431 A1 | 8/2002 | Kajiwara et al. ............... 525/162 |

FOREIGN PATENT DOCUMENTS

| JP | 54-033584 | | 3/1979 | |
| JP | 01-174512 A | | 7/1989 | |
| JP | 06-100607 A | | 4/1994 | |
| JP | 8-319314 A | | 12/1996 | |
| JP | 2002-241412 A | | 8/2002 | |
| JP | 2006-225527 A | | 8/2006 | |
| JP | 2007-126613 A | | 5/2007 | |
| JP | 2007-269863 A | | 10/2007 | |
| JP | 2009-159655 | * | 7/2009 | ............ C08F 263/18 |

OTHER PUBLICATIONS

STN Search Report. Generated on Jul. 15, 2014. pp. 1-37.*
International Search Report mailed May 1, 2013, issued in corresponding International Application No. PCT/JP2012/055340.

* cited by examiner

*Primary Examiner* — Christine T Mui
(74) *Attorney, Agent, or Firm* — Stein IP, LLC

(57) ABSTRACT

Provided is a method for evaluating of the chemical stability of a polychloroprene latex that permits evaluation of the chemical stability of polychloroprene at high accuracy.

First, an aqueous calcium hydroxide or calcium nitrate solution at a concentration of 0.05 to 0.40 mass % is added to a polychloroprene latex having a solid matter concentration of 45 to 65 mass %. The generated precipitate is then collected by filtration and the dry mass is determined, and the precipitation rate (%) is calculated according to the following Formula (I).

$$\text{Precipitation rate (\%)} = \frac{A}{\{B \times (C/100)\}} \times 100 \qquad (I)$$

(wherein, A represents the dry mass (g) of the precipitate; B represents the mass (g) of the polychloroprene latex, and C represents the solid matter concentration (mass %) of the polychloroprene latex.)

7 Claims, No Drawings

METHOD FOR EVALUATING CHEMICAL STABILITY OF POLYCHLOROPRENE LATEX

CROSS-REFERENCE TO RELATED APPLICATIONS

This application is a national stage application of PCT Application No. PCT/JP2012/055340, filed Mar. 2, 2012, which claims the benefit of Japanese Application No. JP 2011-053412, filed Mar. 10, 2011, in the Japanese Patent Office. All disclosures of the document(s) named above are incorporated herein by reference.

BACKGROUND OF THE INVENTION

1. Field of the Invention

The present invention relates to a method for evaluating the chemical stability of a polychloroprene latex. More specifically, it relates to a method for evaluating the chemical stability of a polychloroprene latex used in dip-formed articles such as gloves, boots, and balloons.

2. Description of the Related Art

Polychloroprene latexes have been used as the materials for producing dip-formed articles such as medical gloves, laboratory gloves, catheters, rubber boots, rubber threads, and balloons. These dip-formed articles have been produced mainly by a so-called coagulant solution method, using a three-dimensional former of ceramic or metal. Specifically, a former coated with a coagulant solution, which coagulates polychloroprene latexes, is immersed into and withdrawn from a polychloroprene latex composition blended with sulfur, a vulcanization accelerator and others and then dried, forming a film on the surface. The film is then stripped from the former, to give an article in a particular shape.

In a process for producing dip-formed articles with thin film thickness, such as surgery gloves, there are occasionally problems of coagulation of polychloroprene latex composition during its preparation and cracking and pinhole generation in finished articles. For reduction of such troubles, it is effective to control the stability of the polychloroprene latex to chemicals (chemical stability). For example when the chemical stability of a polychloroprene latex is too low, there may be coagulation when a polychloroprene latex composition is prepared, as it is blended with sulfur or a vulcanization accelerator. Alternatively when the chemical stability is too high, it is not possible to form a uniform film on the former surface, thus leading to easier cracking and pinhole generation thereon.

The chemical stability of a rubber latex is generally determined by mixing the latex with an aqueous inorganic salt solution and measuring the concentration and the dry mass of the coagulum generated (see Patent Documents 1 to 4). For example in the method for producing a polymer latex described in Patent Document 1, determined is the dry mass of the aggregate generated when 5 ml of aqueous 2.5 mass % calcium chloride solution is added to 10 g of a polymer latex prepared by emulsion polymerization of styrene, ethyl acrylate, butyl acrylate, or methyl methacrylate. The ratio of the aggregate to the polymer (mass %) is then determined and used for evaluation of the chemical stability.

Alternatively, Patent Document 2 describes a method of evaluating the chemical stability by determining the amount of the coagulum generated when 5 g of aqueous 0.1-N calcium chloride solution is added dropwise to 100 g of a copolymer latex having a solid matter concentration of 48 mass %, as the mixture is agitated. Yet alternatively, Patent Document 3 describes a method for evaluating the chemical stability by determining the amount of the coagulum generated when aqueous 7 mass % potassium hydroxide solution is added dropwise at a rate of 10% to 100 g of a copolymer latex (solid matter content: 45 mass %) previously filtered.

On the other hand in the method for evaluating the chemical stability described in Patent Document 4, a drop of a latex composition for wet master batch (about 0.2 cm$^3$) was dropped on aqueous sodium chloride solutions different in concentration at an interval of 0.1 mass % and the NaCl solution at the highest concentration in which the latex composition does not solidify is determined.

CITATION LIST

Patent Literatures

[Patent Document 1] Japanese Unexamined Patent Application Publication No. H06-100607
[Patent Document 2] Japanese Unexamined Patent Application Publication No. 2006-225527
[Patent Document 3] Japanese Unexamined Patent Application Publication No. 2007-126613
[Patent Document 4] Japanese Unexamined Patent Application Publication No. 2007-269863

SUMMARY OF THE INVENTION

Technical Problem

However, the methods described above in Patent Documents 1 to 4, which are those for evaluation of latexes of styrene-butadiene rubbers (SBRs) and acrylonitrile-butadiene rubbers (NBRs), have a problem that they cannot be applied to evaluation of polychloroprene latexes.

Polychloroprene latexes for dip-formed articles are produced by emulsion polymerization, using an alkali-soluble rosin acid as emulsifier, and thus stable to alkalinity. In addition, polychloroprene latexes are often blended with an alkaline substance such as sodium hydroxide or calcium hydroxide, for prevention of dehydrochlorination reaction of the chloroprene polymers and the resulting gradual change of pH, when they are stored in an environment exposed to sun light or high temperature for an extended period of time. Thus, polychloroprene latexes are stable in the aqueous potassium hydroxide solution used in Patent Document 3 and resistant to coagulation when it is added thereto.

On the other hand, as described in Patent Documents 1, 2, and 4, when calcium or sodium chloride is used in evaluation of the polychloroprene latex, the coagulation velocity becomes too fast, leading to fluctuation in the amount of the coagulum generated. In addition, use of calcium chloride as coagulant causes a concern that it may corrode the test apparatus that is often made of metal.

Accordingly, an object of the present invention is to provide a method for evaluating the chemical stability of a polychloroprene latex, which permits accurate evaluation of the chemical stability of the polychloroprene.

Solution to Problem

The method for evaluating the chemical stability of a polychloroprene latex according to the present invention comprises the steps of: adding an aqueous calcium hydroxide or calcium nitrate solution at a concentration of 0.05 to 0.40 mass % to a polychloroprene latex having a solid matter concentration of 45 to 65 mass %; collecting the generated precipitate by filtration and measuring the drying mass thereof; and calculating the precipitation rate (%) according to the following Formula 1:

$$\text{Precipitation rate (\%)} = \frac{A}{\{B \times (C/100)\}} \times 100 \quad \text{[Formula 1]}$$

wherein A represents the dry mass of the precipitate (g); B represents the mass of the polychloroprene latex (g); and C represents the solid matter concentration of the polychloroprene latex (mass %).

In the evaluation method, the aqueous calcium hydroxide or calcium nitrate solution can be added in an amount of 50 to 150 g-wet with respect to 100 g-wet of the polychloroprene latex. The term "-wet" means that the value is based on "wet mass."

Alternatively, the polychloroprene latex may contain resin acid and/or ali-metal salts of rosin acid.

Yet alternatively, the chloroprene polymer in the polychloroprene latex is, for example, a copolymer of chloroprene and 2,3-dichloro-1,3-butadiene and the toluene-insoluble matter thereof can be, for example, 70 to 99 mass %.

Advantageous Effects of Invention

It is possible according to the present invention to evaluate the chemical stability of a polychloroprene at high accuracy, as a polychloroprene latex at a particular concentration is mixed with an aqueous calcium hydroxide or calcium nitrate solution at a particular concentration.

Additional aspects and/or advantages of the invention will be set forth in part in the description which follows and, in part, will be obvious from the description, or may be learned by practice of the invention.

DETAILED DESCRIPTION OF THE EMBODIMENTS

Reference will now be made in detail to the present embodiments of the present invention, examples of which are illustrated in the accompanying drawings, wherein like reference numerals refer to the like elements throughout. The embodiments are described below in order to explain the present invention by referring to the tables.

[Method for Evaluating Chemical Stability]

In the evaluation method in an embodiment of the present invention, which is a method for evaluating the stability of a polychloroprene latex to chemicals (chemical stability), an aqueous solution of a particular coagulant is added to a polychloroprene latex and the precipitation rate is calculated from the amount of the precipitate generated. Specifically, the method comprises the following Steps S1 to S3:

(Step S1: Step of Adding Coagulant)

In the evaluation method of the present embodiment, an aqueous calcium hydroxide or calcium nitrate solution at a concentration of 0.05 to 0.40 mass % is first added as aqueous coagulant solution to a polychloroprene latex having a solid matter concentration of 45 to 65 mass %. If a coagulant other than calcium hydroxide and calcium nitrate is used then, there is a concern that the precipitation velocity may become too high, leading to fluctuation in precipitation rate. It is preferable to use calcium hydroxide as the coagulant from the viewpoints of precipitation velocity and dispersibility in the polychloroprene latex and it is thus possible to reduce the fluctuation of the precipitation rate calculated.

In the polychloroprene latex, negatively charged latex particles are emulsified in water. On the other hand, calcium ions in the aqueous solution of the coagulant carry two positive charges. When the calcium ions are brought into contact with the latex particles, these charges are neutralized, leading to instabilization of the emulsion state of latex particles and thus to aggregation of the neighboring particles and precipitation of rubbery lumps.

Lower solid matter concentration of the polychloroprene latex leads to elongation of the distance between latex particles and thus to inhibition of aggregation of the unstabilized particles and precipitation. On the other hand, higher solid matter concentration of the polychloroprene latex leads to decrease of the distance between latex particles and poorer diffusion of the calcium ions added, as they are captured by the aggregate of latex particles close to the site of addition. In such a state, the amount of the generated precipitate fluctuates significantly, resulting in decrease of the reproducibility of the observed value.

Specifically when the solid matter concentration of the polychloroprene latex to be evaluated is less than 45 mass %, the value of the precipitation rate may decline excessively, making the difference in precipitation rate between different samples (polychloroprene latexes) smaller and making it difficult to compare the chemical stabilities. On the other hand when the solid matter concentration of the polychloroprene latex is more than 65 mass %, it becomes difficult to mix the latex uniformly with the aqueous coagulant solution instantaneously, resulting in decrease of the measurement accuracy of the precipitation rate.

Alternatively when the concentration of the aqueous calcium hydroxide or calcium nitrate solution added to the latex is less than 0.05 mass %, the value of the precipitation rate may decline excessively, making the difference in precipitation rate between different samples (polychloroprene latexes) smaller and making it difficult to compare the chemical stabilities. On the other hand when the concentration of the aqueous calcium hydroxide or calcium nitrate solution is higher than 0.35 mass %, the value of the precipitation rate may become excessively high, also making the difference in precipitation rate between different samples (polychloroprene latexes) smaller and making it difficult to compare the chemical stabilities.

The amount of the aqueous coagulant solution, i.e., aqueous calcium hydroxide or calcium nitrate solution, is not particularly limited, but preferably 50 to 150 g-wet with respect to 100 g-wet (wet mass) of the polychloroprene latex to be evaluated. It is thus possible to improve the accuracy of the values of the precipitation rate observed.

The method of adding the aqueous calcium hydroxide or calcium nitrate solution is desirably a method of dropping the aqueous solution from a burette little by little, while the polychloroprene latex is agitated, although it is not particularly limited thereto. If the agitating velocity is too high then, specifically if the agitating velocity is more than 800 rpm, the polychloroprene latex may be lost by scattering. On the contrary if the agitating velocity is too low, specifically if the agitating velocity is less than 200 rpm, it is not possible to mix them homogeneously, leading to fluctuation of the precipitation rate. Thus, the agitating velocity of the polychloroprene latex is preferably 200 to 800 rpm.

In addition, the temperature of the polychloroprene latex and the aqueous calcium hydroxide or calcium nitrate solution is preferably controlled to be constant. If such an aqueous coagulant solution is used, there is almost no influence on the observed value of the precipitation rate, if the temperature thereof is in the range of 5 to 35° C. Thus, the polychloroprene latex or the aqueous calcium hydroxide or calcium nitrate solution is not needed to be cooled or heated, if the measurement temperature is 5 to 35° C.

(Step S2: Step of Filtration and Drying)

The precipitate generated is then collected by filtration and the dry mass is determined. The method of collecting the precipitate by filtration is not particularly limited, but it is possible for example to use a filter paper, a wire mesh having an opening of 300 μm (50 mesh) to 75 μm (200 mesh), or a cloth filter. The precipitate deposited on the agitating blade and the container wall can be collected, for example, with tweezers. The precipitate collected by such a method is then washed with water and dried at a temperature higher than the boiling point of water 100° C. for determination of the dry mass.

(Step S3: Step of Calculating Precipitation Rate)

The precipitation rate (%) is calculated according to the following Formula 2 and the chemical stability of the polychloroprene latex is evaluated, based on the value. When the precipitation rate is lower, which means that the latex particles are more resistant to aggregation, it is considered that the chemical stability is higher. Alternatively when the precipitation rate is higher, which means that the latex particles aggregate more easily, it is considered that the chemical stability is lower. In the following Formula 2, A represents the dry mass (g) of the precipitate; B represents the mass (g) of the polychloroprene latex, and C represents the solid matter concentration (mass %) of the polychloroprene latex.

$$\text{Precipitation rate (\%)} = \frac{A}{\{B \times (C/100)\}} \times 100 \qquad \text{[Formula 2]}$$

[Polychloroprene Latex]

The "polychloroprene latex" to be evaluated in the evaluation method of the present embodiment is a latex (emulsion) prepared by emulsifying a chloroprene polymer, in water, using an emulsifier. The chloroprene polymer is a homopolymer of 2-chloro-1,3-butadiene (hereinafter, referred to as chloroprene) or a copolymer of chloroprene and other monomers. The monomers copolymerizable with chloroprene include, for example, 2,3-dichloro-1,3-butadiene, 1-chloro-1,3-butadiene, sulfur, methacrylic acid and the esters thereof, acrylic acid and the esters thereof and the like. These compounds can be used alone or in combination of two or more.

In the evaluation method in the present embodiment, the chloroprene polymer contained in the polychloroprene latex is preferably a copolymer of chloroprene and 2,3-dichloro-1,3-butadiene and it is possible with the copolymer to provide a dip-formed article with flexibility. When the chloroprene polymer is a copolymer of chloroprene and 2,3-dichloro-1,3-butadiene, the amount of 2,3-dichloro-1,3-butadiene used is preferably 2 to 20 parts by mass with respect to 100 parts by mass of all monomers. A polychloroprene latex containing 2,3-dichloro-1,3-butadiene in an amount in the range above gives more uniform precipitation amount and more reproducible data in evaluation of the chemical stability.

On the other hand, the chloroprene polymer contained in the polychloroprene latex can be prepared by radical emulsion polymerization of chloroprene alone or a mixture of chloroprene and other monomers in water, using an emulsifier. The polymerization temperature then is not particularly limited, but preferably 5 to 50° C. for smooth progress of the polymerization reaction.

The emulsifier used during the emulsion polymerization is not particularly limited and may be any emulsifier, if selected properly. Typical examples of such anionic emulsifiers include carboxylic acid- and sulfate ester-based emulsifiers such as alkali-metal salts of rosin acids, alkyl sulfonates having a carbon number of 8 to 20, alkylaryl sulfates, condensates of sodium naphthalenesulfonate and formaldehyde, and the like.

Typical examples of the nonionic emulsifiers include polyvinylalcohol and the copolymers thereof (e.g., copolymers with acrylamide), polyvinylether and the copolymers thereof (e.g., copolymers with maleic acid), polyoxyethylene alkyl ethers, polyoxyethylene alkyl phenols, sorbitan fatty acid esters, polyoxyethylene acyl esters and the like. Typical examples of the cationic emulsifiers include aliphatic amine salts, aliphatic quaternary ammonium salt such as octadecyltrimethylammonium chloride, dodecyltrimethylammonium chloride, dilauryldimethylammonium chloride, and the like.

In particular among these emulsifiers, a rosin acid and/or an alkali metal salt thereof is used favorably. Specifically, the chloroprene latex evaluated by the evaluation method in the present embodiment preferably contains a rosin acid and/or an alkali-metal salt of a rosin acid. Such a polychloroprene latex is resistant to deposition of the precipitate on test apparatuses such as agitator and thus to removal of the precipitate, permitting evaluation of the chemical stability at high accuracy. The "rosin acid," as used herein, is a mixture for example of resin acids and fatty acids and the composition varies according to the collection method for the rosins, which are classified for example into gum rosin, wood rosin, and tall rosin, the production site of pine, the kinds of the woods, the distillation and purification method, and the disproportionation reaction.

The resin acids contained in the rosin acid include abietic acid, neoabietic acid, palustric acid, pimaric acid, isopimaric acid, dehydroabietic acid, dihydropimaric acid, dihydroisopimaric acid, secodehydroabietic acid, dihydroabietic acid and the like. Alternatively, the fatty acids contained in the rosin acid include oleic acid, linoleic acid and the like. In the evaluation method in the present embodiment, the composition of the rosin acid contained in the polychloroprene latex to be evaluated is not particularly limited.

The blending amount of the rosin acid and/or the alkali-metal salt thereof during emulsion polymerization is desirably 0.5 to 20 parts by mass with respect to 100 parts by mass of all monomers initially introduced. A polychloroprene latex having a blending amount of the rosin acid and/or the alkali-metal salt thereof at less than 0.5 part by mass may form the precipitate before addition of the coagulant only by mechanical shear, making it difficult to evaluate the chemical stability. Alternatively, a polychloroprene latex having a blending amount of the rosin acid and/or the alkali-metal salt thereof at more than 20 parts by mass may foam easily when agitated, causing a concern that the observed value of the precipitation amount may fluctuate significantly.

The initiator used in the emulsion polymerization is not particularly limited and, for example, a persulfate salt such as potassium persulfate or an organic peroxide such as t-butyl hydroperoxide may be used.

The kind of the chain-transfer agent is also not particularly limited and any chain-transfer agent used normally in emulsion polymerization of chloroprene can be used. Specifically, known chain-transfer agents including long-chain alkyl mercaptans such as n-dodecylmercaptan and tert-dodecylmercaptan; dialkylxanthogen disulfides such as diisopropylxanthogen disulfide and diethylxanthogen disulfide; and iodoform can be used favorably.

The terminator (polymerization inhibitor) is also not particularly limited and, for example, 2,6-tertiary-butyl-4-methylphenol, phenothiazine, hydroxy amine or the like can be used.

The final polymerization rate is not particularly limited, but can be controlled arbitrarily in the range of 70 to 100%. Removal of the unreacted monomer (monomer removal) can be performed by any known method, for example by heating under reduced pressure. The polymer structure of the chloroprene polymer is not particularly limited. It is possible to control the molecular weight, molecular weight distribution, gel content, molecular terminal structure, and crystallization velocity of the chloroprene polymer obtained, by selecting, for example, the polymerization temperature, polymerization initiator, chain-transfer agent, terminator, and polymerization rate adequately.

On the other hand, the chloroprene polymer contained in the polychloroprene latex to be evaluated preferably has a toluene-insoluble matter (gel content) of 70 to 99 mass %. It is possible at the gel content above to suppress fluctuation of the precipitation rate and perform evaluating at higher accuracy. As a latex sample having a smaller toluene-insoluble matter is tackier, it deposits easily on the agitating blade during evaluation of the chemical stability, possibly increasing the fluctuation of the value of precipitation rate.

[Applications of Polychloroprene Latex]

The polychloroprene latex to be evaluated by the method for evaluating chemical stability according to the present embodiment is used for production by coagulant solution method of dip-formed articles such as medical gloves, laboratory gloves, catheters, rubber boots, rubber threads and balloons. In the coagulant solution method, used is a latex composition containing a polychloroprene latex and additionally sulfur, metal oxides, thickeners, vulcanization accelerators, aging inhibitors, fillers, and others. A three-dimensional ceramic or metal former previously coated with a coagulant solution on the surface thereof is immersed into and withdrawn from the latex composition described above and the film formed thereof is dried under heat and stripped from the former, to give an article in a particular shape.

Typical examples of the metal oxides blended to the polychloroprene latex include zinc oxide (zinc white), magnesium oxide and the like. The metal oxide may be blended in the powder shape if the chloroprene latex is highly viscous, but preferably blended in the emulsion form, as it is emulsified or dispersed in water, using an emulsifier.

Typical examples of the thickeners include organic thickeners such as polyvinylalcohol (PVA), methylcellulose (MC), hydroxyethylmethylcellulose (HEMC), hydroxypropylmethylcellulose (HPMC), carboxymethylcellulose (CMC), polyacrylic acid-based thickeners, polyacrylamide-based thickeners, and HEUR-based thickeners (polyethylene oxide polymers with both terminals blocked with hydrophobic groups), inorganic thickeners such as silicate compounds (e.g., hectolite and montmorillonite). HEUR-based thickeners, which show high thickening action at a smaller addition amount and are superior in viscosity stability after blending, are favorable among these thickeners.

Examples of the vulcanization accelerators include thiourea-based compounds, dithiocarbamate salts, xanthate salts and the like. Typical examples of the thiourea-based compounds include ethylene thiourea, dibutylthiourea, dilaurylthiourea, N,N'-diphenylthiourea, trimethylthiourea (TMU), N,N'-diethylthiourea (EUR) and the like. Examples of the dithiocarbamate salts include zinc dimethyldithiocarbamate, zinc diethyldithiocarbamate, zinc dibutylthiocarbamate, zinc N-pentamethylene dithiocarbamate, zinc dibenzyldithiocarbamate, copper (II) dimethyldithiocarbamate, iron (III) dimethyldithiocarbamate, tellurium (IV) dimethyldithiocarbamiate and the like. Examples of the xanthate salts include zinc butylxanthate, zinc isopropylxanthate, gallium (III)ethylxanthate and the like.

The aging inhibitors include amine ketone-, aromatic amine-, monophenol-, bisphenol-, and polyphenol-based aging inhibitors and the like. Typical examples of the amine ketone-based aging inhibitors include 2,2,4-trimethyl-1,2-dihydroquinoline polymers, 6-ethoxy-1,2-dihydro-2,2,4-trimethylquinoline, reaction products of diphenylamine and acetone and the like.

Typical examples of the aromatic amine-based aging inhibitors include N-phenyl-1-naphthylamine, octylated diphenylamine, 4,4'-bis($\alpha,\alpha$-dimethylbenzyl)diphenylamine, p-(p-toluenesulfonylamide)diphenylamine, N,N'-di-2-naphthyl-p-phenylenediamine, N,N'-diphenyl-p-phenylenediamine, N-phenyl-N'-isopropyl-p-phenylenediamine, N-phenyl-N'-(1,3-dimethylbutyl)-p-phenylenediamine, N-phenyl-N'-(3-methacryloyloxy-2-hydroxy propyl)-p-phenylenediamine and the like.

Typical examples of the monophenol-based aging inhibitors include 2,6-di-tert-butyl-4-methylphenol, mono (di- or tri)-($\alpha$-methylbenzyl)phenol and the like. Typical examples of the bisphenol-based aging inhibitors include 2,2-methylenebis(4-ethyl-6-tert-butylphenol), 2,2'-methylenebis(4-methyl-6-tert-butylphenol), 4,4'-butylidenebis(3-methyl-6-tert-butylphenol), 4,4'-thiobis(3-methyl-6-tert-butylphenol), butylation reaction products of p-cresol and dicyclopentadiene and the like.

Typical examples of the polyphenol-based aging inhibitors include 2,5-di-tert-butylhydroquinone and 2,5-di-tert-amylhydroquinone. These aging inhibitors are preferably blended, as they are emulsified or dispersed in water using an emulsifier. It is possible in this way to disperse the aging inhibitor in the polychloroprene latex uniformly.

Examples of the fillers include aluminum hydroxide, talc, mica, sericite, kaolin, bentonite, silica, Shirasu balloons, calcium carbonate, barium sulfate, and barium titanate.

On the other hand, in the process for producing dip-formed articles using a polychloroprene latex, for example a solution of an inorganic compound (such as calcium nitrate, aluminum chloride, zinc chloride, calcium chloride, and zinc acetate) or an organic acid (such as formic acid or acetic acid) dissolved in water and/or alcohol is used as the coagulant solution. In the case of the coagulant solution method, such a coagulant solution is applied and dried on the surface of a former, to form a coagulant layer. If the concentration of the coagulant in the solution is low, it may not be possible to apply the coagulant uniformly on the surface of the former or the time needed for drying may be elongated.

Thus, the coagulant concentration in the coagulant solution is generally made higher at 5 to 50 mass %. However, a coagulant solution at such a high concentration cannot permit detection of the fluctuation in chemical stability at high sencxsitivity, as it has an excessively strong action to precipitate the polymer component in the polychloroprene latex. Thus, the coagulant solution traditionally used in the production process for dip-formed articles cannot be used, as it is, for evaluation of chemical stability. In addition, as calcium hydroxide, which is used as the coagulant in the evaluation method in the present embodiment, is less soluble in water, it is not used in the production process for dip-formed articles.

[Method of Using Precipitation Rate]

Use of the precipitation rate, as determined by the evaluation method in the present embodiment, can prevent production of defective articles. It is possible, for example, to prevent cracking and pinhole generation in articles, by determining the relationship between the incidence rates of cracking and pinhole generation in dip-formed articles such as gloves and the chemical stability of the raw material polychloroprene latex (precipitation rate, as determined by the evaluation method in the present embodiment), and by monitoring and controlling the precipitation rate of the raw material polychloroprene latex.

As described above in detail, when the evaluation method in the present embodiment, wherein an aqueous calcium hydroxide or calcium nitrate solution at a concentration of 0.05 to 0.40 mass % is added to a polychloroprene latex having a solid matter concentration of 45 to 65 mass %, is employed, the fluctuation of the observed values is smaller and the processability thereof is also favorable. It is therefore possible to evaluate the chemical stability of a polychloroprene latex easily and accurately.

EXAMPLES

Hereinafter, the advantageous effects of the present invention will be described specifically with reference to Examples and Comparative Examples of the present invention. In the present Example, the chemical stability of the two kinds of polychloroprene latexes shown below (latexes A and B) were evaluated, using each of the aqueous coagulant solutions prepared in Examples and Comparative Examples, as the kind and the concentration of the coagulant is altered.

<Preparation of Latex A>

First, water: 100 parts by mass, a disproportionated rosin acid: 4 parts by mass, sodium hydroxide: 1.3 parts by mass, and sodium salt of formaldehyde naphthalenesulfonic acid condensate: 0.8 part were placed in a reactor having a capacity of 3 liter under nitrogen stream, and these were dissolved. Then, chloroprene: 90 parts by mass, 2,3-dichloro-1,3-butadiene: 10 parts by mass, and n-dodecylmercaptan: 0.03 part by mass were added thereto, while it is agitated. The mixture was polymerized under nitrogen environment at 35° C., using potassium persulfate as initiator, and an emulsion of phenothiazine was added thereto to terminate the polymerization when the polymerization rate reached 85%.

A nonionic surfactant polyoxyethylene laurylether (manufactured by Kao Corp. Emulgen 150): 0.9 part by mass was added to the polymerization solution and unreacted monomers were removed under reduced pressure. The solution was then concentrated, as water was evaporated under reduced pressure, to give polychloroprene latexes (latexes A) each having a solid matter concentration of 40.0 mass %, 55.0 mass %, and 70.0 mass %. The gel content (toluene-insoluble matter) in each polychloroprene latex was found to be 94 mass %, independently of the solid matter concentration after concentration. The solid matter concentration and the gel content were determined in the following manners:

(Solid Matter Concentration)

The solid matter concentration (mass %) was determined according to the following Formula 3. In the following Formula 3, "a" represents the mass (g) of aluminum pan; "b" represents the mass (g) of the aluminum pan carrying 2 ml of polychloroprene latex; and "c" represents the mass (g) of the polychloroprene latex-carrying pan after drying at 125° C. for 1 hour.

$$\text{Solid matter concentration (mass \%)} = \frac{c-a}{b-a} \times 100 \quad \text{[Formula 3]}$$

(Gel Content)

The gel content (toluene-insoluble matter) was determined according to the following Formula 4. In the following Formula 4, "d" represents the mass (g) of the polychloroprene latex after it is freeze-dried. "e" represents the mass (g) of the polychloroprene latex prepared by dissolving it in toluene at 23° C. for 20 hours to a concentration of 0.6 mass %, separating the gel by a centrifugal separator and also, using a wire mesh having an opening of 200 mesh, and drying the gel under air at 110° C. for 1 hour.

$$\text{Gel content (mass \%)} = \frac{d}{e} \times 100 \quad \text{[Formula 4]}$$

<Preparation of Latex B>

Polychloroprene latexes (latexes B) having solid matter concentrations of 40.0 mass %, 55.0 mass %, and 70.0 mass % were prepared in a manner and conditions similar to the latexes A above, except that the addition amount of the polyoxyethylene laurylether (manufactured by Kao Corp. Emulgen 150) was reduced to 0.6 part by mass. The gel content (toluene-insoluble matter) of each polychloroprene latex was found to be 91%, independently of the solid matter concentration after concentration.

<Evaluation of Chemical Stability>

50 g of latex A or B was placed in a glass bottle having a capacity of 225 ml in a room conditioned at 23° C. and 50 g of the aqueous coagulant solution shown in Table 1 or 2 was added dropwise through a burette over a period of 2 minutes, while the solution was agitated at 400 rpm. After addition of all aqueous coagulant solution, the deposit on the agitating blade was all scraped off into the glass bottle, and the solution was left still, as the glass bottle was sealed tightly, for 16 hours. The precipitate was collected by filtration with a 80-mesh wire mesh and cut into fine pieces with scissors, washed with water, and dried at 110° C. for 3 hours. The dry mass of the precipitate was determined and the precipitation rate was calculated according to Formula 2 above. This procedure was repeated 10 times and the average, the standard deviation, and the coefficient of variation of the precipitation rate were calculated. The results are summarized in Tables 1 and 2.

TABLE 1

|  | Example | | | | | | | |
| --- | --- | --- | --- | --- | --- | --- | --- | --- |
|  | 1 | 2 | 3 | 4 | 5 | 6 | 7 | 8 |
| Polychloroprene latex | | | | | | | | |
| Kind | A | A | A | A | B | B | B | B |
| Concentration (mass %) | 55.0 | 55.0 | 55.0 | 55.0 | 55.0 | 55.0 | 55.0 | 55.0 |
| Sample amount (g) | 50.0 | 50.0 | 50.0 | 50.0 | 50.0 | 50.0 | 50.0 | 50.0 |

TABLE 1-continued

|  | Example | | | | | | | |
|---|---|---|---|---|---|---|---|---|
|  | 1 | 2 | 3 | 4 | 5 | 6 | 7 | 8 |
| Aqueous coagulant solution | | | | | | | | |
| Coagulant | $Ca(OH)_2$ | $Ca(OH)_2$ | $Ca(NO_3)_2$ | $Ca(NO_3)_2$ | $Ca(OH)_2$ | $Ca(OH)_2$ | $Ca(NO_3)_2$ | $Ca(NO_3)_2$ |
| Concentration (mass %) | 0.10 | 0.15 | 0.10 | 0.30 | 0.10 | 0.15 | 0.10 | 0.30 |
| Amount added dropwise (g) | 50.0 | 50.0 | 50.0 | 50.0 | 50.0 | 50.0 | 50.0 | 50.0 |
| Precipitation rate (%) | | | | | | | | |
| $n = 1$ | 0.8 | 1.3 | 1.3 | 3.9 | 1.3 | 2.0 | 2.6 | 5.4 |
| $n = 2$ | 0.7 | 1.2 | 1.1 | 3.0 | 1.1 | 2.2 | 2.5 | 5.7 |
| $n = 3$ | 0.8 | 1.2 | 1.3 | 4.2 | 1.3 | 2.5 | 1.9 | 4.0 |
| $n = 4$ | 0.7 | 1.3 | 1.2 | 3.4 | 1.3 | 2.3 | 2.0 | 5.1 |
| $n = 5$ | 0.7 | 1.1 | 1.2 | 3.5 | 1.1 | 2.2 | 2.3 | 4.8 |
| $n = 6$ | 0.6 | 1.3 | 1.1 | 3.6 | 1.0 | 2.1 | 2.1 | 4.7 |
| $n = 7$ | 0.7 | 1.2 | 1.3 | 4.1 | 1.2 | 2.0 | 2.0 | 4.9 |
| $n = 8$ | 0.7 | 1.2 | 1.5 | 3.1 | 1.1 | 2.7 | 2.3 | 5.0 |
| $n = 9$ | 0.7 | 1.2 | 1.2 | 3.8 | 1.3 | 2.3 | 2.2 | 4.6 |
| $n = 10$ | 0.7 | 1.4 | 1.2 | 3.6 | 1.0 | 2.1 | 2.2 | 5.1 |
| Average | 0.7 | 1.2 | 1.2 | 3.6 | 1.2 | 2.2 | 2.2 | 4.9 |
| Standard deviation | 0.06 | 0.08 | 0.12 | 0.39 | 0.13 | 0.22 | 0.22 | 0.46 |
| Coefficient of variation | 0.08 | 0.07 | 0.09 | 0.11 | 0.11 | 0.10 | 0.10 | 0.09 |

TABLE 2

|  | Comparative Example | | | | | | | | | | | |
|---|---|---|---|---|---|---|---|---|---|---|---|---|
|  | 1 | 2 | 3 | 4 | 5 | 6 | 7 | 8 | 9 | 10 | 11 | 12 |
| Polychloroprene latex | | | | | | | | | | | | |
| Kind | A | A | B | B | A | A | A | A | B | B | A | A |
| Concentration (mass %) | 55 | 55 | 55 | 55 | 55 | 55 | 40 | 70 | 40 | 70 | 55 | 55 |
| Sample amount (g) | 50 | 50 | 50 | 50 | 50 | 50 | 50 | 50 | 50 | 50 | 50 | 50 |
| Aqueous coagulant solution | | | | | | | | | | | | |
| Coagulant | $CaCl_2$ | $CaCl_2$ | $CaCl_2$ | $CaCl_2$ | $CaCl_2$ | $Ca(NO_3)_2$ | $Ca(NO_3)_2$ | $Ca(NO_3)_2$ | $Ca(NO_3)_2$ | $Ca(NO_3)_2$ | $Ca(NO_3)_2$ | $Ca(NO_3)_2$ |
| Concentration (mass %) | 0.1 | 0.3 | 0.1 | 0.3 | 4 | 4 | 0.15 | 0.15 | 0.15 | 0.15 | 0.01 | 0.45 |
| Amount added dropwise (g) | 50 | 50 | 50 | 50 | 50 | 50 | 50 | 50 | 50 | 50 | 50 | 50 |
| Precipitation rate (%) | | | | | | | | | | | | |
| $n = 1$ | 7.8 | 8.5 | 8.1 | 12.1 | 88.3 | 98.9 | 2.5 | 32 | 2.9 | 41.4 | 0 | 9 |
| $n = 2$ | 8.5 | 9.5 | 10.6 | 10.8 | 97 | 88.7 | 2.7 | 33.8 | 3 | 48.6 | 0.1 | 6.5 |
| $n = 3$ | 7 | 13.3 | 8.2 | 11 | 99.6 | 99.7 | 3 | 35 | 2.4 | 52 | 0.2 | 7.1 |
| $n = 4$ | 9.2 | 12 | 11 | 12.5 | 99 | 99.8 | 2.3 | 20 | 2.3 | 32.1 | 0.1 | 6.2 |
| $n = 5$ | 7.4 | 10.7 | 11.4 | 9.7 | 94.8 | 99.2 | 3 | 34.2 | 2.7 | 21.1 | 0 | 6.6 |
| $n = 6$ | 10.1 | 14 | 8.7 | 12 | 99.2 | 99 | 2.5 | 51.3 | 2.2 | 23 | 0.1 | 7.3 |
| $n = 7$ | 8 | 12.4 | 9.4 | 11.6 | 100 | 98.5 | 2.7 | 40.6 | 2.8 | 35.8 | 0.1 | 7.5 |
| $n = 8$ | 9.4 | 14.3 | 9.5 | 10.7 | 99.3 | 100 | 2.9 | 26.8 | 2.6 | 23.9 | 0.1 | 8.3 |
| $n = 9$ | 8.8 | 11.4 | 10.8 | 8.4 | 91.8 | 92 | 2.3 | 44.4 | 2.8 | 44 | 0 | 6 |
| $n = 10$ | 9.3 | 8.1 | 8.9 | 15 | 99 | 93.4 | 2.4 | 54.8 | 2.7 | 50 | 0 | 8.4 |
| Average | 8.6 | 11.4 | 9.7 | 11.4 | 96.8 | 96.9 | 2.6 | 37.3 | 2.6 | 37.2 | 0.1 | 7.3 |
| Standard deviation | 0.99 | 2.2 | 1.21 | 1.76 | 3.96 | 4.02 | 0.27 | 10.69 | 0.26 | 11.75 | 0.07 | 1.01 |
| Coefficient of variation | 0.12 | 0.19 | 0.13 | 0.15 | 0.04 | 0.04 | 0.1 | 0.29 | 0.1 | 0.32 | 0.96 | 0.14 |

Latex B is expected to have chemical stability lower and precipitation rate higher than those of latex A, as it contains a smaller amount of the nonionic surfactant. However as shown in Table 2, there was no difference in precipitation rate between the latex A and the latex B by the evaluation method of Comparative Examples 1 to 4, wherein calcium chloride was used as the coagulant. In contrast by the evaluation methods of Examples 1 to 8 in Table 1, there was difference in precipitation rate between the latex A and the latex B, thus permitting evaluation of the chemical stability.

In addition in the case of the evaluation methods of Comparative Example 5 to 6 and 11 to 12, because the concentration of the aqueous coagulant solution was outside the range of 0.05 to 0.40 mass %, it was not possible to evaluate the chemical stability accurately, as the entire latex coagulated or the polymer component precipitated, leading to increase of the fluctuation of the value of precipitation rate. Further in the case of the evaluation methods of Comparative Examples 7 to 10, because the solid matter concentration of the polychloroprene latex was outside the range of 45 to 65 mass %, there was no difference in precipitation rate between the latex A and the latex B, prohibiting comparison of the chemical stability. Alternatively in the case of the evaluation methods of Examples 1 to 8, there was small fluctuation of the value of precipitation rate, permitting accurate evaluation of the chemical stability.

The results above confirm that it is possible according to the evaluation method of the present invention to evaluate the chemical stability of a polychloroprene latex at high accuracy.

Although a few embodiments of the present invention have been shown and described, it would be appreciated by those skilled in the art that changes may be made in this embodiment without departing from the principles and spirit of the invention, the scope of which is defined in the claims and their equivalents.

The invention claimed is:

1. A method for evaluating of the chemical stability of a polychloroprene latex, comprising the steps of:
    adding an aqueous calcium hydroxide or calcium nitrate solution at concentration of 0.05 to 0.40 mass % to a polychloroprene latex having a solid matter concentration of 45 to 65 mass %;
    collecting the generated precipitate by filtration and measuring the dry mass thereof; and,
    calculating the precipitation rate (%) according to the following Formula:

$$\text{Precipitation rate } (\%) = \frac{A}{\{B \times (C/100)\}} \times 100$$

wherein A represents the dry mass of the precipitate (g); B represents the mass of the polychloroprene latex (g); and C represents the solid matter concentration of the polychloroprene latex (mass %), and wherein the chloroprene polymer in the polychloroprene latex has a toluene-insoluble matter of 70 to 99 mass %.

2. The method for evaluating the chemical stability of a polychloroprene latex according to claim 1, wherein the aqueous calcium hydroxide or calcium nitrate solution is added in an amount of 50 to 150 g-wet with respect to 100 g-wet of the polychloroprene latex.

3. The method for evaluating the chemical stability of a polychloroprene latex according to claim 1, wherein the polychloroprene latex contains a rosin acid and/or an alkali-metal salt of the rosin acid.

4. The method for evaluating the chemical stability of a polychloroprene latex according to claim 1, wherein the chloroprene polymer in the polychloroprene latex is a copolymer of chloroprene and 2,3-dichloro-1,3-butadiene.

5. The method for evaluating the chemical stability of a polychloroprene latex according to claim 2, wherein the polychloroprene latex contains a rosin acid and/or an alkali-metal salt of the rosin acid.

6. The method for evaluating the chemical stability of a polychloroprene latex according to claim 2, wherein the chloroprene polymer in the polychloroprene latex is a copolymer of chloroprene and 2,3-dichloro-1,3-butadiene.

7. The method for evaluating the chemical stability of a polychloroprene latex according to claim 3, wherein the chloroprene polymer in the polychloroprene latex is a copolymer of chloroprene and 2,3-dichloro-1,3-butadiene.

* * * * *